(12) United States Patent
Han et al.

(10) Patent No.: US 7,190,461 B2
(45) Date of Patent: *Mar. 13, 2007

(54) METHOD AND APPARATUS FOR DETERMINING A BIDIRECTIONAL REFLECTANCE DISTRIBUTION FUNCTION, SUBSURFACE SCATTERING OR A BIDIRECTIONAL TEXTURE FUNCTION OF A SUBJECT

(75) Inventors: Jefferson Y. Han, Holliswood, NY (US); Kenneth Perlin, New York, NY (US)

(73) Assignee: New York University, New York, NY (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/858,665

(22) Filed: Jun. 1, 2004

(65) Prior Publication Data

US 2005/0068537 A1 Mar. 31, 2005

Related U.S. Application Data

(63) Continuation-in-part of application No. 10/620,920, filed on Jul. 16, 2003.

(60) Provisional application No. 60/396,697, filed on Jul. 17, 2002, provisional application No. 60/476,320, filed on Jun. 6, 2003.

(51) Int. Cl.
*G01N 21/47* (2006.01)
*G01N 21/55* (2006.01)

(52) U.S. Cl. ........................... 356/446; 356/445

(58) Field of Classification Search ......... 356/445–446
See application file for complete search history.

(56) References Cited

U.S. PATENT DOCUMENTS 5,637,873 A * 6/1997 Davis et al. ............ 250/339.11
6,122,042 A * 9/2000 Wunderman et al. ......... 356/73

FOREIGN PATENT DOCUMENTS

DE 10143602 A1 * 4/2003

OTHER PUBLICATIONS

U.S. Appl. No. 10/620,920.*
U.S. Appl. No. 10/665,804.*

* cited by examiner

*Primary Examiner*—Hwa (Andrew) Lee
*Assistant Examiner*—Amanda Merlino
(74) *Attorney, Agent, or Firm*—Ansel M. Schwartz

(57) ABSTRACT

An apparatus for determining a bidirectional reflectance distribution function of a subject. In one embodiment, the apparatus includes a light source for producing light. The apparatus includes means for measuring the bidirectional reflectance distribution function of the subject from multiple locations simultaneously with the light. A method for determining a bidirectional reflectance distribution function of a subject.

26 Claims, 5 Drawing Sheets

METHOD AND APPARATUS FOR DETERMINING A BIDIRECTIONAL REFLECTANCE DISTRIBUTION FUNCTION, SUBSURFACE SCATTERING OR A BIDIRECTIONAL TEXTURE FUNCTION OF A SUBJECT

The present invention is a continuation-in-part of U.S. patent application No. 10/620,920 filed on Jul. 16, 2003, which claims priority from U.S. provisional application 60/396,697 filed on Jul. 17, 2002.

This application claims the benefit of U.S. Provisional Application No.: Application No. 60/476,320 filing date Jun. 06, 2003

FIELD OF THE INVENTION

The present invention is related to determining a bidirectional reflectance distribution function of a subject. More specifically, the present invention is related to determining a bidirectional reflectance distribution function of a subject using a kaleidoscope.

BACKGROUND OF THE INVENTION

Much recent work in realistic image synthesis has focused on the use of actual data measurements of real-world surfaces and materials, both in the search for better data-driven reflectance models, and for direct use in image-based rendering techniques.

The reflectance properties of a surface can be characterized by its Bidirectional Reflectance Distribution Function (BRDF) [NICODEMUS, F. E., RICHMOND, J. C., AND HSIA, J. J. 1977. Geometric Considerations and Nomenclature for Reflectance, U.S. Dept. of Commerce, National Bureau of Standards, Oct. 1977, incorporated by reference herein], the four dimensional function that describes how much light from any incident direction $(\theta_i, \phi_i)$ is transferred to any exitant direction $(\theta_e, \phi_e)$:

$$BRDF(\theta_i, \phi_i, \theta_e, \phi_e)$$

The field is quite mature in techniques for measuring BRDFs, and for representing them accurately and compactly. Real world surfaces, however, are not perfectly homogeneous—they exhibit local variations in microgeometry and in reflectance, which are not adequately represented by a single BRDF.

Dana et al. define the Bidirectional Texture Function (BTF) as the six dimensional function which extends the BRDF by allowing reflectance to vary spatially along the surface, parameterized by (u,v) DANA, K. J., GINNEKEN, B. VAN, NAYAR, S. K., AND KOENDERINK, J. J. 1999. Reflectance and Texture of Real World Surfaces. ACM Transactions on Graphics, 18, 1, 1–34, incorporated by reference herein:

$$BRDF (u, v, \theta_i, \phi_i, \theta_e, \phi_e)$$

This representation is able to effectively capture the various subtleties of complexly textured surfaces, particularly those exhibiting such phenomena as self-occlusion and self-shadowing.

There have been recent advances in working with BTFs for realistic image synthesis. Because the BTF is a large unwieldy 6D function, it is difficult to obtain a dense sampling, and therefore current databases are relatively sparse. Yet recent successful research has shown that even a sparse sampling of the BTF can be adequate for rendering applications. LIU, X., YU, Y., AND SHUM, H. Y. 2001. Synthesizing Bidirectional Texture Functions for Real-World Surfaces. In Proceedings of ACM SIGGRAPH 2001, ACM Press/ACM SIGGRAPH, New York. E. Fiume, Ed., Computer Graphics Proceedings, Annual Conference Series, ACM, 97–106; TONG, X., ZHANG, J., LIU, L., WANG, X., GUO, B., AND SHUM, H. Y. 2002. Synthesis of Bidirectional Texture Functions on Arbitrary Surfaces. ACM Transactions on Graphics, 21, 3, 665–672; VASILESC, M. A. O., AND TERZOPOULOS, D. 2003. TensorTextures. ACM SIGGRAPH 2003 Conference Abstracts and Applications, Jul. 2003, all of which are incorporated by reference herein.

Increased quality of BTF sample data would also be of benefit to computer vision research. For example, algorithms that reconstruct geometry or motion from multiple views require correspondences to be found between these views. BTF data would allow robust testing of the identification of corresponding surface points, even as the appearance of each surface point varies with view angle. This data would also benefit shape-from-texture, texture segmentation, and texture recognition techniques.

Use of real-world reflectance is currently characterized by the difficulty of gathering the BRDF and the BTF, particularly due to the high dimensionality of this data.

The straightforward approach to measuring the 4D BRDF is to mechanically position a light source and photometer around the hemisphere about the sample though the use of robotic armatures, as in Murray-Coleman and Smith. MURRAY-COLEMAN, J. F., AND SMITH, A. M. 1990. The Automated Measurement of BRDFs and their Application to Luminaire Modeling. Journal of the Illuminating Engineering Society, pp. 87–99, Winter 1990, incorporated by reference herein. Any such mechanical arrangement must have four degrees of freedom; data collection is tediously performed by sequentially stepping through each position.

Subsequent methods greatly improve the efficiency of data acquisition by reducing the number of mechanically scanned dimensions through the use of a 2D imaging element such as a CCD camera. Ward's LBL imaging gonioreflectometer uses a hemi-ellipsoidal mirror. WARD, G. J. 1992. Measuring and Modeling Anisotropic Reflection. In Computer Graphics (Proceedings of ACM SIGGRAPH 92), 26, 2, ACM, 255–263, incorporated by reference herein. A CCD camera equipped with a wide-angle-lens, and the surface sample are positioned at the mirror's two respective foci to effectively map pixel position to exitant angular position. This method requires mechanical repositioning of the light source. Also notable about Ward's device is that the mirror is semi-transparent, thereby permitting measurements when view and illumination angles are coincident. Others have thoroughly explored the various other possible arrangements of curved mirrors and beam splitters. DAVIS, K. J., AND RAWLINGS, D. C. 1997. Directional reflectometer for measuring optical bidirectional reflectance. U.S. Pat. No. 5,637,873, June 1997; MATTISON, P. R., DOMBROWSKI, M. S., LORENZ, J., DAVIS, K., MANN, H., JOHNSON, P., AND FOOS, B. 1998. Hand-held directional reflectometer: an angular imaging device to measure BRDF and HDR in real-time. In Proceedings of SPIE, The International Society for Optical Engineering, Scattering and Surface Roughness II, 3426:240–251, Jul. 1998; and CARTER, R. R., AND PLESKOT, L. K. 1999. Imaging scatterometer. U.S. Pat. No. 5,912,741, Jun. 1999, all of which are incorporated by reference herein.

An alternative way to utilize an imaging element is to measure the BRDF on a curved sample. Lu et al. arranges a sample patch onto a known cylinder. LU, R., KOEN- DERINK, J. J., AND KAPPERS, A. M. L. 1998. Optical properties (bidirectional reflectance distribution functions) of velvet. Applied Optics, 37, 25, 5974–5984, incorporated by reference herein. Marschner et al. relaxes the sample geometry restriction by utilizing a range scanner, and improves acquisition flexibility by allowing for free positioning of the capture camera. MARSCHNER, S. R., WESTIN, S. H., LAFORTUNE, E. P. F., TORRANCE, K. E., AND GREENBERG, D. P. 1999. Image-based BRDF Measurement Including Human Skin. In Proceedings of the 10th Eurographics Workshop on Rendering, pp. 131–144, Jun. 1999, incorporated by reference herein.

More recent work attempts to recover the BRDF from sampling environments that are even less structured. Boivin and Gagalowicz demonstrate recovering multiple BRDFs from a single photograph, with known geometry and light source positions. BOIVIN, S. AND GAGALOWICZ, A. 2001. Image-Based Rendering of Diffuse, Specular and Glossy Surfaces from a Single Image. In Proceedings of ACM SIGGRAPH 2001, ACM Press/ACM SIGGRAPH, New York. E. Fiume, Ed., Computer Graphics Proceedings, Annual Conference Series, ACM, 107–116, incorporated by reference herein. Ramamoorth and Hanrahan describe a signal processing framework that generalizes the recovery of the BRDF under unknown lighting conditions. RAMAMOORTHI, R. ANDHANRAHAN, P. 2001. A Signal-Processing Framework for Inverse Rendering. In Proceedings of ACM SIGGRAPH 2001, ACM Press/ACM SIGGRAPH, New York. E. Fiume, Ed., Computer Graphics Proceedings, Annual Conference Series, ACM, 117–128, incorporated by reference herein.

The seminal work by Dana et al. on the BTF [1999] presents a 3DOF robotic system that incrementally tilts/rotates a patch of the sample in front of a light source. This method produces 205 total samples of the BTF, with a relatively even distribution of illumination directions, but, due to mechanical limitations, with a limited distribution of viewing angles. It also requires a sample patch of the surface to be affixed to the device, which makes in situ measurements impossible, particularly for skin.

Other research involving BTFs utilizes various other custom gantry rigs, such as that of Furukawa et al., which uses 2 motorized concentric arcs carrying 6 cameras and 6 lights. FURUKAWA, R., KAWASAKI, H., IKEUCHI, K., AND SAKAUCHI, M. 2002. Appearance based object modeling using texture database: Acquisition, compression and rendering. In Proceedings of the 13th Eurographics Workshop on Rendering Techniques, pp. 257–266, 2002, incorporated by reference herein.

Later work by Dana introduces a BTF measurement device that utilizes a concave paraboloid mirror section, similar to that used in previous BRDF capture devices, but in concert with an aperture and a translation stage for the sample. DANA, K. J. 2001. BRDF/BTF Measurement Device. In Proceedings of Eighth IEEE International Conference on Computer Vision (ICCV), IEEE Computer Society, vol. 2, pp. 460–6, Vancouver, British Columbia, Jul. 2001, incorporated by reference herein. Theoretically, this technique should be able to produce very high resolution sampling of the BTF in every dimension, with large flexibility in sample distribution, but at a slow capture rate. It also inherits the problems associated with the need to affix surface samples.

Note that this technique is representative of a general class of solutions to the BTF capture problem, which utilize a 4D BRDF measurement device, mechanically scanning the sample across the device to obtain the additional two dimensions.

Other techniques measure that subset of the BTF for which the viewpoint is fixed, and only illumination is varied.

Debevec et al.'s "Light Stage", constructed to capture the complex reflectance of the human face, mechanically scans a directional light source at relatively high speeds through two degrees of freedom, capturing 64×32 illumination samples. DEBEVEC, P., HAWKINS, T., TCHOU, C., DUIKER, H. P., SAROKIN, W., AND SAGAR, M. 2000. Acquiring the Reflectance Field of a Human Face. In Proceedings of ACM SIGGRAPH 2000, ACM Press/ACM SIGGRAPH, New York. Computer Graphics Proceedings, Annual Conference Series, ACM, 145–156, incorporated by reference herein. Successive versions of the stage have replaced this single light source, first with a linear array of xenon strobes on a motorized arc, and then with a static 2D array of 156 LED clusters, allowing for the capture of subjects in motion under arbitrary illumination conditions. DEBEVEC, P., WENGER, A., TCHOU, C., GARDNER, A., WAESE, J., AND HAWKINS, T. 2002. A Lighting Reproduction Approach to Live-Action Compositing. ACM Transactions on Graphics, 21, 3, 547–556, incorporated by reference herein.

Malzbender et al. describes a device for in situ surface reflectance measurement, wherein 50 inward-pointing light sources are distributed on a small, portable hemispherical frame, allowing for rapid automated acquisition. MALZBENDER, T., GELB, D., AND WOLTERS, H. 2001. Polynomial Texture Maps. In Proceedings of ACM SIGGRAPH 2001, ACM Press/ACM SIGGRAPH, New York. E. Fiume, Ed., Computer Graphics Proceedings, Annual Conference Series, ACM, 519–528, incorporated by reference herein. Polynomial curves are fitted to the lighting-dependent color at each pixel; these curves are used to generate images with novel lighting conditions that interpolate the light positions that were sampled.

SUMMARY OF THE INVENTION

The present invention pertains to an apparatus for determining a bidirectional reflectance distribution function of a subject. The apparatus comprises a light source for producing light. The apparatus comprises means for measuring the bidirectional reflectance distribution function of the subject from multiple locations simultaneously with the light.

The present invention pertains to an apparatus for determining a bidirectional reflectance distribution function of a subject. The apparatus comprises a light source for producing light. The apparatus comprises means for measuring the bidirectional reflectance distribution function of the subject from more than 1 camera or more than 1 projector.

The present invention pertains to a method for determining a bidirectional reflectance distribution function of a subject. The method comprises the steps of producing light from a light source. There is the step of measuring the bidirectional reflectance distribution function of the subject from multiple locations simultaneously with the light.

The present invention pertains to an apparatus for determining sub-surface scattering of a subject. The apparatus comprises a light source for producing light. The apparatus comprises means for measuring the sub-surface scattering of the subject.

The present invention pertains to a method for determining sub-surface scattering of a subject. The method comprises the steps of producing light from a light source. There is the step of measuring the sub-surface scattering of the subject.

The present invention pertains to an apparatus for determining sub-surface scattering of a subject. The apparatus comprises a light source for producing light. The apparatus comprises, for a set of incoming light directions and a set of outgoing light directions for each of a set of surface points in regard to the subject; of the light which enters the subject from any incoming light direction from the set of incoming light directions, into any surface point A of the set of surface points, means for measuring a proportion of the light that exits out of the subject in any outgoing light direction of the set of outgoing light directions from surface point B, where points A and B can be either a same point or different points.

The present invention pertains to a method for determining sub-surface scattering of a subject. The method comprises the steps of producing light from a light source. There is the step of, for a set of incoming light directions and a set of outgoing light directions for each of a set of surface points in regard to the subject; of the light which enters the subject from any incoming light direction from the set of incoming light directions, into any surface point A of the set of surface points, measuring a proportion of the light that exits out of the subject in any outgoing light direction of the set of outgoing light directions from surface point B, where points A and B can be either a same point or different points.

BRIEF DESCRIPTION OF THE DRAWINGS

In the accompanying drawings, the preferred embodiment of the invention and preferred methods of practicing the invention are illustrated in which.

DETAILED DESCRIPTION

Figure 2:
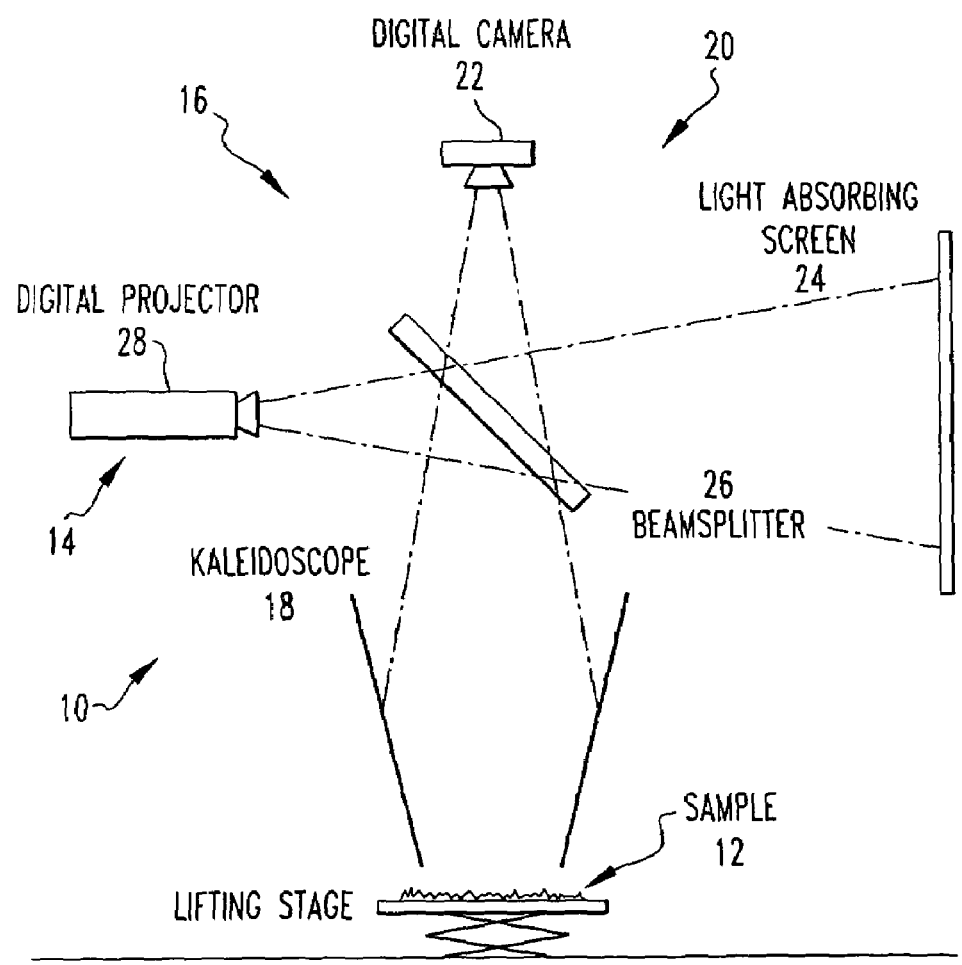
FIG. 2 is a schematic representation of the apparatus of the present invention.

Referring now to the drawings wherein like reference numerals refer to similar or identical parts throughout the several views, and more specifically to FIG. 2 thereof, there is shown an apparatus 10 for determining a bidirectional reflectance distribution function of a subject 12. The apparatus 10 comprises a light source 14 for producing light. The apparatus 10 comprises means for measuring the bidirectional reflectance distribution function of the subject 12 from multiple locations simultaneously with the light.

Preferably, the measuring means 16 includes a kaleidoscope 18. The measuring means 16 preferably includes sensing means 20 for sensing the light from the subject 12. Preferably, the sensing means 20 includes a camera 22 which receives light from the subject 12. The camera 22 is positioned so a path of the light from the subject 12 and the light source 14 are merged.

The sensing means 20 preferably includes a light absorbing screen 24 which receives light from the subject 12. Preferably, the sensing means 20 includes a beam splitter 26 disposed between the camera 22 and a light absorbing screen 24 which allows the light from the subject 12 to be received by both the camera 22 and the light absorbing screen 24. The light source 14 preferably includes a digital projector 28.

The present invention pertains to an apparatus 10 for determining a bidirectional reflectance distribution function of a subject 12. The apparatus 10 comprises a light source 14 for producing light. The apparatus 10 comprises means for measuring the bidirectional reflectance distribution function of the subject 12 from more than 1 camera 22 or more than 1 projector.

The present invention pertains to a method for determining a bidirectional reflectance distribution function of a subject 12. The method comprises the steps of producing light from a light source 14. There is the step of measuring the bidirectional reflectance distribution function of the subject 12 from multiple locations simultaneously with the light.

The present invention pertains to an apparatus 10 for determining sub-surface scattering of a subject 12. The apparatus 10 comprises a light source 14 for producing light. The apparatus 10 comprises means for measuring the sub-surface scattering of the subject 12.

The present invention pertains to a method for determining sub-surface scattering of a subject 12. The method comprises the steps of producing light from a light source 14. There is the step of measuring the sub-surface scattering of the subject 12.

The present invention pertains to an apparatus 10 for determining sub-surface scattering of a subject 12. The apparatus 10 comprises a light source 14 for producing light. The apparatus 10 comprises, for a set of incoming light directions and a set of outgoing light directions for each of a set of surface points in regard to the subject 12; of the light which enters the subject 12 from any incoming light direction from the set of incoming light directions, into any surface point A of the set of surface points, means for measuring a proportion of the light that exits out of the subject 12 in any outgoing light direction of the set of outgoing light directions from surface point B, where points A and B can be either a same point or different points.

The present invention pertains to a method for determining sub-surface scattering of a subject 12. The method comprises the steps of producing light from a light source 14. There is the step of, for a set of incoming light directions and a set of outgoing light directions for each of a set of surface points in regard to the subject 12; of the light which enters the subject 12 from any incoming light direction from the set of incoming light directions, into any surface point A of the set of surface points, measuring a proportion of the light that exits out of the subject 12 in any outgoing light direction of the set of outgoing light directions from surface point B, where points A and B can be either a same point or different points.

In the operation of the invention, the apparatus 10 is based on the principle of the kaleidoscope 18. BREWSTER, D. 1819. A Treatise on the Kaleidoscope, A. Constable, incorporated by reference herein. Generally used as a child's toy, a kaleidoscope 18 is a hollow tube of polygonal cross-section, whose inner walls are lined with front-surface mirrors. Peering into a kaleidoscope 18 creates an infinite "hall of mirrors" illusion; any surface sample placed at the far end will appear to "multiply" into many replicated images of itself.

Figure 1:
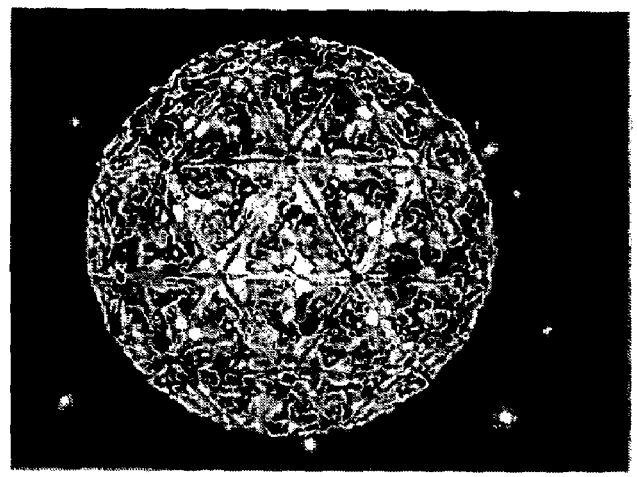
FIG. 1 is a view through a kaleidoscope.

A kaleidoscope 18 can be tapered, so that its far end is smaller than its near end. When this is done, the surface sample at the far end will look like a faceted virtual sphere. This is because each successive reflection reorients the reflected image of the surface a little further away from the perpendicular, until eventually the reflected images disappear over the horizon of the sphere [FIG. 1].

The effect is analogous to having an entire array of cameras 22 all pointing toward the surface sample from different directions, which is precisely what is needed to measure the BTF. A single camera 22 pointed at a surface sample which is on the far end of a tapered kaleidoscope 18 will be able to see that same surface sample simultaneously from many different angles. These differently angled views of the surface sample appear to the camera 22 as different facets of the virtual sphere.

A nice benefit of this approach is that it can also be used as an illumination technique, using a single projector to illuminate the same surface sample from many different directions. When a projector is pointed down into the tapered kaleidoscope 18, different pixels of the projected image will arrive at the sample after having reflected off the kaleidoscope 18 walls in different ways, and therefore will approach the sample from various directions. In effect, different regions of the projected image behave like separate light sources. By keeping only selected pixels of the projected image bright, a particular direction from which to illuminate the sample can be chosen.

The optical paths of the camera 22 and projector need to be merged together, so that both can be pointed down into the kaleidoscope 18. This is done through the use of a 45° beam splitter 26. Light from the projector reflects off this beam splitter 26 down into the kaleidoscope 18. Light emerging back out of the kaleidoscope 18 is transmitted through the beam splitter 26 and is then captured by the camera 22. This arrangement allows the projected image to be coaxial with the image seen by the camera 22. FIG. 2 shows an optical schematic of the device.

Measurement of the surface BTF proceeds by taking a sequence of successive sub-measurements, one after the other. During each submeasurement, exactly one region of the illumination image is bright, and all others are dark. Because each region of the illumination image corresponds to a unique sequence of reflections of light off of the kaleidoscope 18 walls, that region will illuminate the surface sample from a unique sub-range of incoming light directions. A complete measurement consists of successive illumination of the sample surface by each of the illumination regions in turn.

This approach has a number of advantages in comparison to previous methods for measuring the BTF. This approach requires no moving parts, allowing for full measurement to be performed very quickly. Since no physical movement is required between submeasurements, all submeasurements are guaranteed to be perfectly registered to one another. This property allows for a quite significant improvement in accuracy over previous approaches.

The apparatus 10 can be used to measure surfaces in situ, under any lighting conditions, without relocating the sample from its native setting. For some site-specific surfaces, such as living human skin, methods in current use for measuring BTF are simply not viable, since they all require isolating a sample into a light-controlled environment. Also, approaches that require the sample to be physically repositioned between measurements cannot be used to measure loose samples such as rice, dirt or pebbles.

This approach requires only a single CCD camera 22 or equivalent image capture device. This property allows the device to be fabricated at a low cost in comparison with previous methods that require multiple CCD cameras or equivalent image capture devices. This approach richly samples the BTF. Even the first prototype of the present invention captured 484 illumination/view angle pairs, which exceeds the 205 pairs captured by the technique of Dana et al. DANA, K. J., GINNEKEN, B. VAN, NAYAR, S. K., AND KOENDERINK, J. J. 1999. Reflectance and Texture of Real World Surfaces. ACM Transactions on Graphics, 18, 1, 1–34, incorporated by reference herein. The technique is also versatile enough to allow the device to be portable and hand-held.

All of these qualities make for a valuable new measurement tool, for use in situations for which current techniques are too bulky or unwieldy, or are simply impossible. For example, during a motion picture production, a member of the visual effects crew could use the apparatus 10 to measure the BTF of the skin of various parts of an actor's face, or the fabric of a costume or couch, or any prop or desk, wall, or floor surface of the set. With this information in hand, the appearance of these items can then be duplicated digitally with highly convincing realism and fidelity. Once the entire BTF has been captured, the filmmaker is free to make arbitrary decisions about lighting and camera 22 placement, which the virtual objects can be synthesized to match.

The kaleidoscope 18 approach to BTF measurement is an extremely flexible one, with many design parameters to consider, depending on the objective.

Figure 3A:
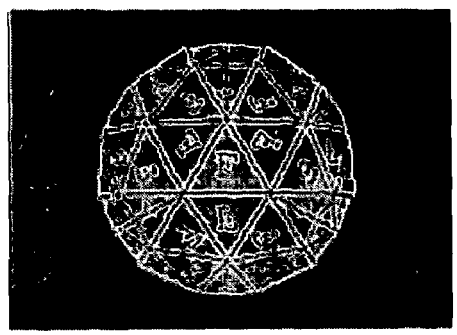
FIG. 3 shows kaleidoscope simulations for n={3,4,6}.
Figure 3B:
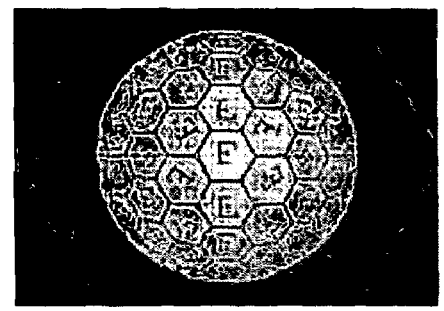
Figure 3C:
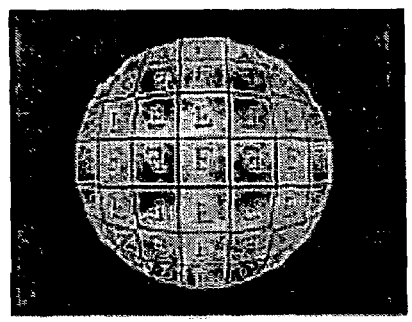

In general, the kaleidoscope 18 can be made as a regular polygon of n sides, for n>=3. A ray-tracer was implemented to better understand the effects of various values of n (see FIG. 3).

It is apparent that not every virtual facet is complete; many are fragmented, appearing to have real and virtual mirror seams slicing through them. For simplicity, only the unfragmented facets were considered as usable data. As a result, the effect of n on fragmentation is a major factor in kaleidoscope 18 design, since the proportion of these facets varies with n.

The value of n also directly determines the shape of the base as the regular n-gon. However, image processing is most easily performed on rectangular images, so for any n!=4, only the area of the largest inscribable square is utilized.

Triangular n=3 case was ultimately used, because of its simplicity in construction, and its highest proportion of whole unfragmented facets, though it does compromise on sample area and capture efficiency.

Varying the angle of taper also significantly affects what is seen through the kaleidoscope 18. Angle of taper refers to the amount that the kaleidoscope 18 narrows from one end to the other, and is defined as the tilt angle between the mirrored side and the kaleidoscope's optical axis.

A larger taper angle causes each successive reflection to tilt further away from the surface normal, which produces fewer facets that are visible before eventually disappearing over the horizon (elevation exceeds 90°). Conversely, a smaller angle of taper, forming a kaleidoscope 18 with walls that are more parallel, produces a greater number of visible facets with finer angular steps. However, capturing a greater number of facets in a single view results in fewer pixels for each facet, and thus a reduction in spatial resolution.

Kaleidoscopes with a relatively large angle of taper (and correspondingly fewer, larger facets) are used to capture relief surfaces with high self-shadowing, such as pebbles, cloth, and jellybeans. This optimizes for greater spatial resolution within the sample; the tradeoff is fewer different angular directions. Tall slender kaleidoscopes 18 with a smaller angle of taper are used (and correspondingly more numerous, smaller facets) to capture shiny surfaces with sharp specular peaks in reflectance. An optimal taper angle given a desired angular resolution, and desired final grazing angle can be calculated.

Figure 4:
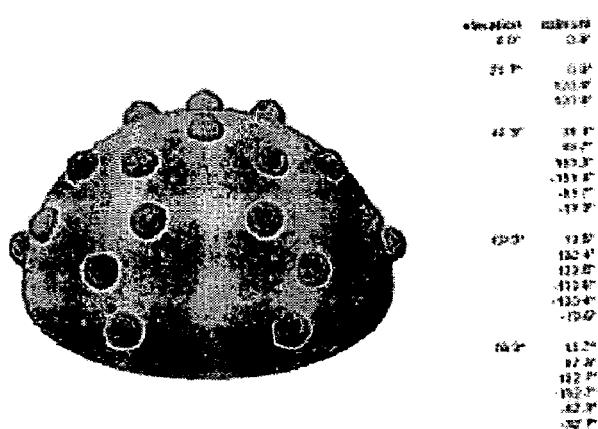
FIG. 4 shows the distribution of viewpoint and illumination angles.

Ultimately, a taper that tilts from vertical angle by 9° was chosen. This provides 4 orders of reflections to the horizon, a final grazing facet elevation angle of 76°, and 22 complete views of the surface sample, providing $22^2=484$ distinct view/illumination angle pairs. See FIG. 4 for a tabulation of the actual angles of this design, along with a visualization of those spherical coordinates on the unit hemisphere.

The remaining design parameter decisions consist of determining the scale of the kaleidoscope 18 that will best: (i) accommodate a surface sample of a desired size, and (ii) work with a given camera 22 field of view and projector field of view without the use of any additional lenses or optics.

Before constructing the device, a simple OpenGL-based visualization tool to balance the various interrelated parameters was created. This allowed us to vary, in simulation, taper angle, base patch size, kaleidoscope 18 height, and field of view and distance of the camera 22 and the projector.

At this stage, it was realized that for a given sample size and tilt angle (a smaller angle produces a larger virtual sphere), the height of the kaleidoscope 18 (and therefore the bulk and expense of the front-surface mirrors) is determined by the field of view of the camera 22 and projector: the kaleidoscope's height can be reduced if a wider field of view is used. The camera 22 used had a vertical field of view of 39°; the projector had a vertical field of view of 21°. The smaller of these (the projector) was the limiting factor, which ultimately determined the kaleidoscope 18 height.

The kaleidoscope 18 has a triangular base edge length of 4", providing a maximally inscribed active sample area of 2.3" square, and has a total height of 14.7". The three trapezoidal front-surface mirrors needed for this design were cut for us from standard stock by a professional stained glass cutter.

For the beam splitter 26, an ordinary plate of glass was used, which has approximately 96% transmission at a 45° incident angle. Because the projector has a high luminance, this glass reflects more than sufficient illumination down into the kaleidoscope 18.

LCD projectors were generally found to be unsuitable for purposes here, because the reflectivity of the beam splitter 26 varied with polarization. For this reason, experiments were conducted with a DLP projector, which provides unpolarized illuminance. The camera was a Canon PowerShot G1, which has a capture resolution of 2048×1536. A small aperture was maintained so as to maximize depth of focus.

A large proportion of light was transmitted through the beam splitter 26, and ended up being projected onto the wall of the laboratory. Some of this reflected light made its way back to the beam splitter 26, and a small portion of that light was reflected up into the camera 22. A matte black surface was placed on the wall, which absorbed almost all of this unwanted light. The color calibration step compensated for what little was left.

Figure 5:
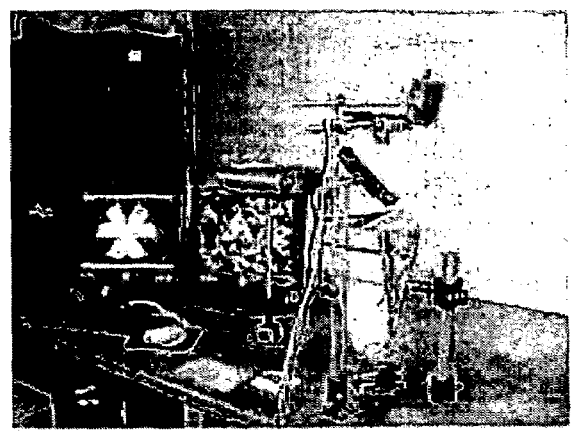
FIG. 5 shows the experimental setup for the apparatus.

To maintain precision in the experiments, it was important not to continually jar the kaleidoscope 18. For this reason, the entire apparatus 10 was installed on an optical table. A sample to be measured was first slid underneath the kaleidoscope 18, upon a mechanical stage. The stage was then elevated until the sample was flush with the kaleidoscope 18 opening. The laboratory setup is shown in FIG. 5.

Deviations in brightness and color balance came from many sources, including mirror coatings, mirror absorption, and mismatch between the projector "white" color and the camera 22 "white" color. In the measurements dichroic mirror coatings caused slight color shifts at different incident angles, which showed up as variations in hue between different facets of the virtual sphere.

There was also a dropoff per unit sample area at the outer facets, simply due to the fact that a tilted facet presents fewer pixels to the projector. An inherent shortcoming is that both spatial resolution and brightness drop off at the most extreme angles.

To compensate for all of these deviations, as well as others not accounted for, the device was calibrated in situ using a Kodak standard color chart. This calibration was only done once, since the projector, camera 22, beam splitter 26 and mirrors all remained unchanged. Over a long time frame, it would be wise to periodically recalibrate to account for gradual shifts in the projector lamp as it ages.

Image processing to identify and extract the many reflected images of the surface sample. This procedure needed to be performed only once, using the following in situ calibration:

A planar 3×3 checkerboard test pattern was placed under the kaleidoscope 18 and performed corner detection to identify the sub-pixel coordinates of each reflected checkerboard image. Those points were used to compute the best homography transform that maps each patch to the unit square.

Those transformations were in turn applied to each of the 22 illumination imaging shots. The resulting 22 square sub-images were each clipped out, and saved to disk. The result was a 22×22 array of images indexed by projector facet and camera 22 facet. Correction for the lens distortion of the camera 22 needed to be done only once, using the technique of Zhang. ZHANG, Z. 1999. Flexible Camera Calibration By Viewing a Plane From Unknown Orientations. International Conference on Computer Vision (ICCV '99), Corfu, Greece, pages 666–673, Sep. 1999, incorporated by reference herein.

It was necessary to determine which pixels in the projected image illuminated each kaleidoscopically reflected image of the surface sample. For purposes of the current work, this was done manually, implementing a triangle editor in software. Using the actual image from a video camera 22 peering into the kaleidoscope 18 as a guide, this editor allowed a user to quickly outline each of the 22 triangles.

Ideally, this step should be done automatically as follows: The projector would project a known tracking pattern, which the camera 22 would record. This data would then be used to recover, in a single step, the projection matrix of the projector itself, as well as all the projection matrices of all the reflected images of the surface sample. This calibration also would need to be performed only once.

Figure 6A:
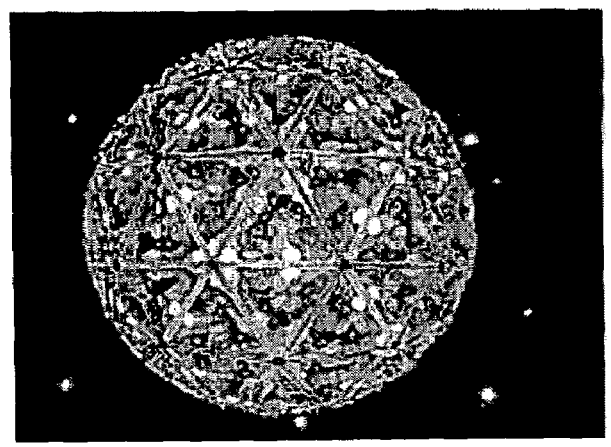
FIG. 6 shows two multi-view captures of "jellybeans", under different illumination directions.
Figure 6B:
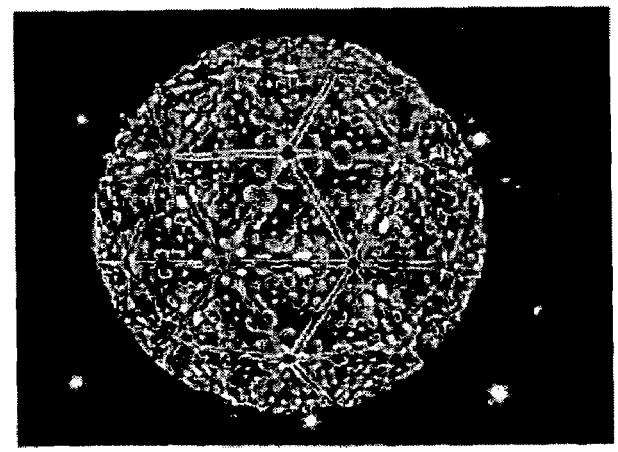
Figure 9:
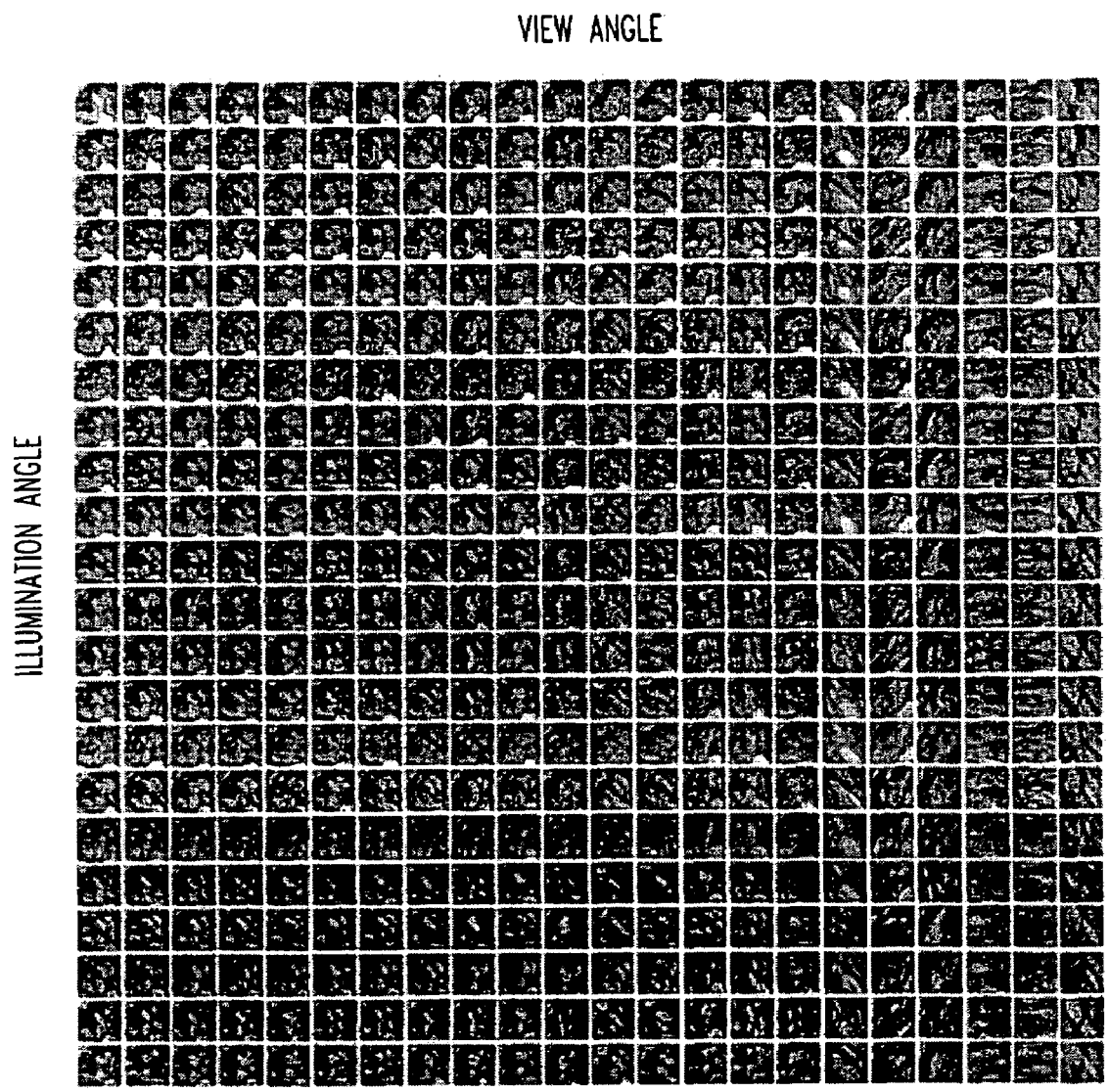
FIG. 9 shows the full 22×22 image BTF measurement of "jellybeans".

FIG. 6 shows two multi-view image captures of a sample of jellybeans, taken with two different illumination angles, and FIG. 9 shows the full, structured 484 image BTF after sub-image extraction has been performed.

Figure 7:
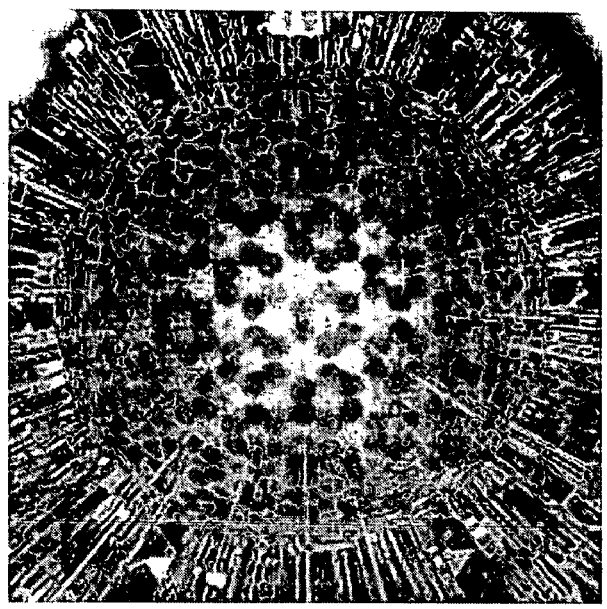
FIG. 7 shows a multi-view image of a penny, using a longer taper kaleidoscope.

FIG. 7 shows a multi-view image of a coin captured with a kaleidoscope 18 having a relatively small taper. This device has 79 unfragmented facets, and can capture $79^2=6241$ distinct view/illumination angle pairs. A small-taper kaleidoscope 18 is particularly useful for measuring fine variations in reflectance due to small differences in angle.

For surfaces which have appreciable sub-surface scattering, it is useful to measure the BSSRDF (Bidirectional Scattering Surface Reflectance Distribution Function) of the surface by illuminating only a small spot of the surface sample, and then to measure the light which emerges from locations within the larger region that surrounds this spot. JENSEN, H. W., MARSCHNER, S. R., LEVOY, M., AND HANRAHAN, P. 2001. A Practical Model for Subsurface Light Transport. In Proceedings of ACM SIGGRAPH 2001, ACM Press/ACM SIGGRAPH, New York. E. Fiume, Ed., Computer Graphics Proceedings, Annual Conference Series, ACM, 511–518, incorporated by reference herein. By incrementally moving this illuminated spot and taking associated measurements at each successive spot position, what can be termed the sample's BSSTF (Bidirectional Scattering Surface Texture Function) can be measured:

$$BSSTF(u_i, v_i, u_e, v_e, \theta_i, \phi_i, \theta_e, \phi_e)$$

The BSSTF, also described as the reflectance field in [Debevec et al. 2001], is an eight dimensional function: two for the entry point of the light into the sample, two for the exit point of the light out of the sample, two for incoming spherical angle, and two for outgoing spherical angle. Because this technique requires no physical movement, it is now feasible to accumulate the many measurements needed to build this eight dimensional function in a timely manner without any loss of precision from mechanical movement.

Figure 8A:
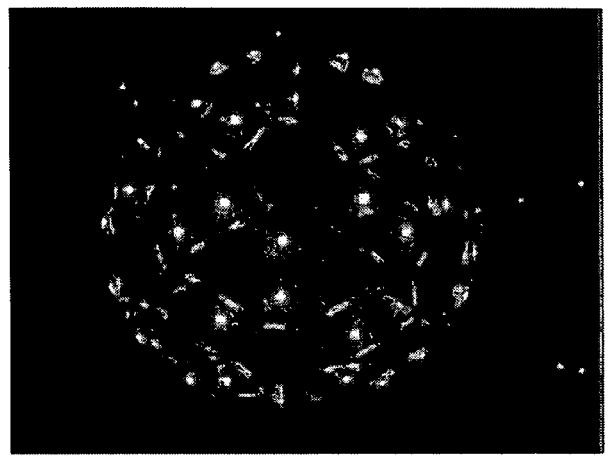
FIG. 8 shows two measurements of a BSSTF.
Figure 8B:
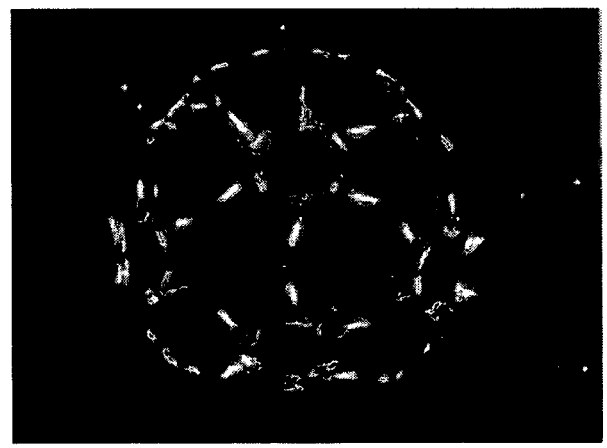

BSSTFs have been measured through the primary kaleidoscope 18. FIGS. 8a and 9b show two sub-steps of a measurement of a translucent block, in these early tests illuminated by a laser. Analogously, the projector would scan an image of a fine spot across the surface sample area.

High dynamic range (HDR) capture capability can be accomplished, by taking multiple image captures of varying exposure lengths, as in Devebec and Malik. DEBEVEC, P. E., MALIK, J. 1997. Recovering High Dynamic Range Radiance Maps from Photographs. In Proceedings of ACM SIGGRAPH 1997, ACM Press/ACM SIGGRAPH, New York. Computer Graphics Proceedings, Annual Conference Series, ACM, 369–378, incorporated by reference herein.

The most generally useful embodiment of the technique would be a small, hand held, battery operated apparatus 10, which would be used in situ to measure surface reflectance in somewhat the way a light meter is currently used to measure illuminance. The apparatus 10 would be held against any surface sample to be captured. The only essential component change will be a replacement of the projector by a set of small individually collimated white light LEDs. Because the apparatus 10 would lie flush against the sample, unwanted ambient light could be excluded from the measurement through the use of a light curtain. This would allow the measurement to be made under uncontrolled lighting conditions. In this embodiment, the technique will have the greatest ability to positively impact the motion picture industry, by helping to reduce costs and increase flexibility for digital set construction and digital actor replacement.

At the other end of the scale, a room-scale version of the apparatus 10 can be implemented. In this arrangement, each wall of a high-ceiling room would be a trapezoidal mirror. A two dimensional array of downward-pointing cameras and projectors would be mounted on the ceiling. This apparatus 10 would provide a relatively economic way to simultaneously capture a live performance from a large number of camera 22 angles under controllable lighting conditions.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for determining one or more values of a bidirectional reflectance distribution function of a subject comprising:
    a light source for producing light; and
    means for measuring one or more values of the bidirectional reflectance distribution function of multiple locations of the subject simultaneously with the light.

2. An apparatus as described in claim 1 wherein the measuring means includes a reflecting arrangement.

3. An apparatus as described in claim 2 wherein the reflecting arrangement includes a kaleidoscope.

4. An apparatus as described in claim 3 wherein the measuring means includes sensing means for sensing the light from the subject.

5. An apparatus as described in claim 4 wherein the sensing means includes a camera which receives light from the subject, the camera positioned so a path of the light from the subject and the light source are merged.

6. An apparatus as described in claim 5 wherein the sensing means includes a light absorbing screen which receives light from the subject.

7. An apparatus as described in claim 6 wherein the sensing means includes a beam splitter disposed between the camera and a light absorbing screen which allows the light from the subject to be received by both the camera and the light absorbing screen.

8. An apparatus as described in claim 7 wherein the light source includes a digital projector.

9. An apparatus for determining one or more values of a bidirectional reflectance distribution function of a subject comprising:
    a light source for producing light; and
    means for measuring one or more values of the bidirectional reflectance distribution function of multiple locations of the subject simultaneously from more than 1 camera or more than 1 projector.

10. An apparatus as described in claim 9 wherein the light source is a DLP projector.

11. An apparatus as described in claim 9 wherein the light source is a white light LED.

12. A method for determining one or more values of a bidirectional reflectance distribution function of a subject comprising the steps of:
    producing light from a light source; and
    measuring one or more values of the bidirectional reflectance distribution function of multiple locations of the subject from multiple locations simultaneously with the light.

13. An apparatus for determining one or more values of a bidirectional texture function of a subject comprising:
    a light source for producing light; and
    means for measuring one or more values of the bidirectional texture function of the subject of multiple locations simultaneously with the light.

14. An apparatus as described in claim 13 wherein the measuring means includes a reflecting arrangement.

15. An apparatus as described in claim 14 wherein the reflecting arrangement includes a kaleidoscope.

16. An apparatus as described in claim 15 wherein the measuring means includes sensing means for sensing the light from the subject.

17. An apparatus as described in claim 16 wherein the sensing means includes a camera which receives light from the subject, the camera positioned so a path of the light from the subject and the light source are merged.

18. An apparatus as described in claim 17 wherein the sensing means includes a light absorbing screen which receives light from the subject.

19. An apparatus as described in claim 18 wherein the sensing means includes a beam splitter disposed between the camera and a light absorbing screen which allows the light from the subject to be received by both the camera and the light absorbing screen.

20. An apparatus as described in claim 19 wherein the light source includes a digital projector.

21. An apparatus for determining one or more values of a bidirectional reflectance distribution function of a subject comprising:
 a light source for producing light; and
 means for measuring one or more values of the bidirectional reflectance distribution function of multiple locations of the subject simultaneously with the light having no moving parts.

22. An apparatus for determining one or more values of a bidirectional reflectance distribution function of a subject comprising:
 a light source for producing light; and
 means for measuring one or more values of the bidirectional reflectance distribution function of multiple locations of the subject simultaneously with the light, the light source and measuring means together being portable and handheld.

23. An apparatus for determining one or more values of a bidirectional texture function of a subject comprising:
 a light source for producing light; and
 a measurer for measuring one or more values of the bidirectional texture function of multiple locations of the subject simultaneously with the light.

24. An apparatus for determining one or more values of a bidirectional reflectance distribution function of a subject comprising:
 a light source for producing light; and
 a measurer for measuring one or more values of the bidirectional reflectance distribution function of multiple locations of the subject simultaneously with the light.

25. An apparatus as described in claim 24 wherein the light source and measurer together being portable and handheld.

26. An apparatus for determining one or more values of a bidirectional reflectance distribution of a subject comprising:
 a light source for producing light; and
 means for measuring one or more values of the bidirectional reflectance distribution of multiple locations of the subject simultaneously with the light.

* * * * *